US007825153B2

(12) United States Patent
Nifantiev et al.

(10) Patent No.: US 7,825,153 B2
(45) Date of Patent: Nov. 2, 2010

(54) PHOTOSENSITIZER FORMULATIONS AND THEIR USE

(75) Inventors: Nikolay Nifantiev, Moscow (RU); Volker Albrecht, Jena (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 11/153,703

(22) Filed: Jun. 15, 2005

(65) Prior Publication Data
US 2006/0035952 A1 Feb. 16, 2006

Related U.S. Application Data

(60) Provisional application No. 60/602,264, filed on Aug. 16, 2004.

(51) Int. Cl.
*A61K 31/409* (2006.01)
(52) U.S. Cl. .................... 514/410; 540/145
(58) Field of Classification Search .......... 514/410, 514/23, 561, 454, 185; 424/423, 450; 540/145
See application file for complete search history.

(56) References Cited

U.S. PATENT DOCUMENTS

| 4,017,501 | A | * | 4/1977 | Gordon et al. | 546/336 |
|---|---|---|---|---|---|
| 4,992,257 | A | | 2/1991 | Bonnett et al. | |
| 5,162,519 | A | * | 11/1992 | Bonnett et al. | 540/145 |
| 5,173,504 | A | * | 12/1992 | Dougherty | 514/410 |
| 5,214,036 | A | * | 5/1993 | Allison et al. | 514/185 |
| 5,399,583 | A | * | 3/1995 | Levy et al. | 514/410 |
| 5,492,924 | A | * | 2/1996 | Gatt et al. | 514/410 |
| 5,576,013 | A | * | 11/1996 | Williams et al. | 424/423 |
| 5,616,342 | A | * | 4/1997 | Lyons | 424/450 |
| 5,877,165 | A | * | 3/1999 | Miura et al. | 514/64 |
| 6,090,788 | A | * | 7/2000 | Lurie | 514/23 |
| 6,270,749 | B1 | | 8/2001 | Blumenkranz et al. | |
| 6,462,192 | B2 | * | 10/2002 | Robinson et al. | 540/145 |
| 6,609,014 | B1 | * | 8/2003 | Allison et al. | 600/310 |
| 6,949,581 | B2 | * | 9/2005 | Nifantiev et al. | 514/410 |
| 6,984,655 | B1 | * | 1/2006 | Mori et al. | 514/410 |
| 7,001,991 | B2 | * | 2/2006 | Faulk | 530/380 |
| 2003/0083649 | A1 | | 5/2003 | Margaron et al. | |
| 2003/0125346 | A1 | * | 7/2003 | Buchanan et al. | 514/275 |
| 2003/0167033 | A1 | | 9/2003 | Chen et al. | |
| 2004/0147500 | A1 | * | 7/2004 | Brun et al. | 514/185 |
| 2004/0259810 | A1 | * | 12/2004 | Grierson et al. | 514/23 |

FOREIGN PATENT DOCUMENTS

WO  WO03/039597  5/2003

OTHER PUBLICATIONS

Desroches et al., Luminescence, 2001, 16, p. 173-178.*
Bonnett et al., J. Porphyrins and Phthalocyanines, 2001, 5, p. 652-661.*
Hamster Biological Values from www.labdiet.com, accessed Jul. 22, 2009.*
Ronn, A.M., et al: "Human Tissue Levels and Plasma Pharmacokinetics of Temoporfin (Foscan, mTHPC)", Lasers in Medical Science 1996, 11:267-272.
Glanzmann, T., et al: "Pharmacokinetics and pharmacodynamics of tetra(m-hydroxyphenyl)chlorin in the hamster cheek pouch tumor model: comparison with clinical measurements." Journal of Photochemistry and Photobiology B: Biology 57 (2000) 22-32.
Annex I, Summary of Product Characteristics: Foscan 1 mg/ml solution for injection, 2006.
Ris H-B, et al: "Photodynamic therapy with mTHPC and polyethylene glycol-derived mTHPC: a comparative study on human tumour xenografts." British Journal of Cancer (1999) 79(7/8), 1061-1066.

* cited by examiner

*Primary Examiner*—Michael G Hartley
*Assistant Examiner*—Nissa M Westerberg
(74) *Attorney, Agent, or Firm*—Bolesh J. Skutnik; BJ Associates

(57) ABSTRACT

A low concentration formulation for hydrophobic photosensitizers (PS) and method for photodynamic therapy ("PDT") using the disclosed low concentration formulations provide for more accurate, more efficient and more convenient dosing. The inventive formulation (1) reduces the time for a therapeutically effective level of photosensitizer to accumulate in diseased tissue and (2) reduces the time for achieving a sufficient ratio of photosensitizer in diseased tissue vs. healthy tissue. The inventive formulation reduces the time interval between PS application/administration and irradiation (the drug-light interval or "DLI") and can provide for a "same day" PDT treatment option. 0.08 mg/ml to 1.3 mg/ml meta Tetra-Hydroxy-Phenyl Chlorin (m-THPC) as the photosensitizer in a mixture of pure propylene glycol and ethanol (3:2 volume ratio) accumulates in diseased tissue and differentiates between diseased tissue and normal tissue sufficiently quickly for 'one day' or overnight administration and activation treatment procedures to be possible.

6 Claims, No Drawings

PHOTOSENSITIZER FORMULATIONS AND THEIR USE

DOMESTIC PRIORITY UNDER 35 USC 119(e)

This application claims the benefit of U.S. Provisional Application Ser. No. 60/602,264, filed Aug. 16, 2004, which is incorporated by reference herein.

BACKGROUND OF THE INVENTION

1. Field of the Invention

The present invention relates to the field of photodynamic therapy, particularly to formulations for improved photodynamic therapy.

2. Information Disclosure Statement

Photodynamic therapy (PDT) has become an increasingly prevalent treatment option for a variety of diseases characterized by hyperproliferative cells, such as cancer and certain skin conditions such as psoriasis. Hyperproliferative epithelial diseases (epidermal and mucosal diseases) are a major health problem and affect nearly everyone at least once during his or her lifetime. Other examples of hyperproliferative epithelial diseases include cutaneous tumors (basal cell carcinoma, squamous cell carcinoma, melanoma), Barrett's esophagus, virus-caused diseases (warts, herpes simplex, condylomata acuminata), premalignant and malignant diseases of the female genital tract (cervix, vagina, vulva), and premalignant and malignant diseases of mucosal tissues (oral, bladder, rectal).

PDT uses photosensitizers (PS) in combination with light irradiation at specific wavelengths to induce oxidative damage in hyperproliferative cells and tissues. It is thought that hyperproliferative tissues selectively retain PS and that subsequently induced cell damage is localized in areas of PS accumulation. Numerous types of photosensitizers have been evaluated and shown to be at least partially effective for PDT. Known PDT photosensitizers include psoralens, porphyrins, chlorins, bacteriochlorins, pheophorbide, bacteriopheophorbide and phthalocyanins, as well as precursors to protoporphyrin IX such as 5-AminoLevulinic Acid (ALA).

In large part, the efficacy of PDT treatment depends on the photochemical, photobiological, and pharmacokinetic/phototherapeutic properties of the photosensitizer (PS). Consequently, the formulation of the PS is a critical factor in the successful photodynamic treatment of hyperproliferative disease. To be therapeutically useful, a PS formulation should deliver the PS in a form that can be readily and selectively internalized by hyperproliferative target cells, while also facilitating accurate and convenient dosing. Known photodynamic medicaments are administered or dosed in milligram quantities relative to kilograms of body weight (mg/kg), however, sub-milligram PS dosing has been proposed for specific vascular treatments and to stimulate wound healing. But, for the treatment of cancerous tissues, it is believed that a similar low dose regime would reduce the effectiveness of PDT, especially for treatments where the PS is administered systemically. As used herein, "low concentration formulation" is defined as a formulation with a substantially reduced PS concentration as compared to known PDT formulations and medicaments. Similarly, "low concentration therapy" refers to any PDT treatment method that administers photosensitizers in a low concentration formulation.

Meta-tetra(hydroxyphenyl)chlorin ("m-THPC"), also known as Temoporfin and by the trade name Foscan®, is a photosensitizer shown to be effective in PDT of cancer, especially for advanced head and neck squamous cell carcinoma. The recommended dose for m-THPC is 0.15 mg/kg of body weight, and is provided in a 4 mg/ml solution for administration via intravenous injection.

Some other commonly used porphyrins for photodynamic therapy are Hematoporphyrin IX (HpIX), Hematoporphyrin derivative (HpD) and various HpD preparations such as Photofrin® (porfimer sodium, Axcan Pharma PDT Inc.). For the treatment of esophageal cancer and endobronchial non-small cell cancer, Photofrin® has a recommended dose of 2 mg/kg of body weight, which is administered by injection after reconstituting dried Photofrin® in a 2.5 mg/ml solution. Photogem®, another hematoporphyrin derivative, has a recommended dose of 1-2 mg/kg of body weight, which is administered by injection from a 5 mg/ml stock solution.

However, known photodynamic medicaments suffer from the relatively unselective uptake and retention of the PS by hyperproliferative cells, which results in the destruction of normal tissues during the PDT irradiation cycle. Furthermore, high concentration PS formulations increase the incidence, severity, and duration of side effects such as generalized post-treatment skin and eye photosensitivity, as well as treatment site irritation and pain.

The general photosensitization of the skin and eyes after treatment with PS is a well documented side-effect of conventional photodynamic therapy, and is especially common in PDT methods requiring the systemic administration of photosensitizers. After such treatments, the patient experiences a generalized skin photosensitivity which creates the risk of a widespread and severe erythema (skin redness) if the patient is exposed to visible light. In treatment regimes where photosensitizers are topically applied, the treatment area will remain photosensitized for 6 weeks or more. During any period of general or local photosensitivity, patients must avoid sunlight and bright indoor light to allow the photosensitizer to clear from the skin and blood stream. Patients must also wear protective clothing and sunglasses when outdoors.

Another side-effect associated with conventional PDT treatment, is injection site irritation and pain. It is very common for patients to experience a burning feeling or other unpleasant sensations at the site of PS injection during the administration of photodynamic medicaments. Other known post-treatment complications at the site of PS administration include phlebitis, lymphangitis and chemical burns. Although PDT is much less traumatic than other cancer treatments, including chemotherapy and certain radiation therapies, a convenient and cost-effective strategy for reducing the incidence and/or severity of PDT specific side-effects is needed.

U.S. Pat. Nos. 4,992,257 and 5,162,519 disclose the use of select dihydro-porphyrins and tetrahydro porphyrins, including m-THPC, in combination with light irradiation (652-653 nm) to induce necrosis (tissue death) in tumors. In particular, these references describe the depth of tumor necrosis that results when m-THPC is dosed at 0.5 mg/kg as compared to 0.255 mg/kg. Specifically, these references teach that the depth of tumor necrosis increases by 43% when m-THPC is administered at the higher dose (5.41±0.39 mm and 3.79±0.28 mm, respectively).

U.S. Pat. No. 6,609,014 describes a "low dose PDT" method limited to the treatment of restenosis and intimal hyperplasia in blood vessels. The reference defines "low dose PDT" as a total photodynamic experience at substantially lower levels of intensity than ordinarily employed and teaches a method comprised of three variables, namely photosensitizer concentration, light dose and time of irradiation. Moreover, the reference teaches that an increase in one variable permits a decrease in another. As such, this reference does not teach the effect of photosensitizer dose outside and independent from changes in irradiation dose or other parameters. Nor does this reference teach the significance of photosensitizer concentration in the context of treating other hyperproliferative tissues or cell types with PDT.

U.S. Pat. No. 5,399,583 discloses a limited group of hydromonobenzoporphyrins, or "green porphyrins," which are photoactive at wavelengths of 670-780 nm. This wavelength of light is thought to penetrate deeper into body tissues which may allow for the use of lower doses of green porphyrins in PDT. Further, this reference discloses doses ranging from 0.1 mg/kg to 10 mg/kg for the claimed green porphyrin compounds, but does not describe the effect of photosensitizer concentration for this or other classes of photo sensitizers.

The prior art described above does not teach nor anticipate the impact of reducing photosensitizer concentration on cytotoxicity. Moreover, there remains a need for PS formulations that are more efficient and have fewer and/or less severe side-effects than known PDT methods and formulations. The present invention addresses these needs.

OBJECTIVES AND BRIEF SUMMARY OF THE INVENTION

It is an object of the present invention to provide a photosensitizer formulation that results in faster concentration of photosensitizers in hyperproliferative tissue and differentiation from normal tissues in the body.

It is another object of the present invention to provide a photosensitizer formulation and photodynamic therapy method that reduces the interval between photosensitizer administration and irradiation (the drug-light interval or "DLI").

It is yet another object of the present invention to provide a photosensitizer formulation that can be less traumatically administered to patients than known PS compositions.

It is a still further object of the present invention to provide a photosensitizer formulation that results in fewer or less severe side-effects than known photosensitizer compositions and methods.

Briefly stated, the present invention discloses a low concentration formulation for hydrophobic photosensitizers (PS) and improved method for photodynamic therapy ("PDT"). It was found that PDT treatments using the disclosed low concentration formulations provide for more accurate, more efficient and more convenient dosing. It was found that the inventive formulation (1) reduces the time for a therapeutically effective level of photosensitizer to accumulate in diseased tissue and (2) reduces the time for achieving a sufficient ratio of photosensitizer in diseased tissue vs. healthy tissue. As a result, the formulation of the invention reduces the time interval between PS application/administration and irradiation (the drug-light interval or "DLI") and can provide for a "same day" PDT treatment option. The inventive formulation can be used for PDT treatment regimes where photosensitizers are administered in at least one preselected dose, including a low concentration therapy for PDT. In particular, when meta Tetra-Hydroxy-Phenyl Chlorin (m-THPC) is the photosensitizer then a concentration of 0.8 mg/ml to 0.04 mg/ml in a mixture of pure propylene glycol and ethanol in a 3:2 volume ratio accumulates in diseased tissue and differentiates between diseased tissue and normal tissue sufficiently quickly for 'one day' or overnight administration and activation treatment procedures to be possible.

The above, and other objects, features and advantages of the present invention will become apparent from the following description.

DETAILED DESCRIPTION OF PREFERRED EMBODIMENTS

The present invention is a result of the surprising discovery that photodynamic therapy ("PDT") using low concentration formulations of photosensitizers can be more efficient than PDT treatments using known photosensitizer concentration formulations and provide useful enhancements over the standard practice. As a result, the present invention offers significant advantages over conventional photodynamic medicaments and standard PDT treatments. Advantages of the present invention include: an improved rate of preferential photosensitizer accumulation in hyperproliferative tissue; a reduced time for achieving a therapeutically effective amount of photosensitizer in diseased tissue; and a reduction in the incidence and severity of PDT side-effects such as treatment site discomfort and skin and eye photosensitivity;. The present invention significantly reduces the time interval between photosensitizer administration and irradiation (the "drug-light interval" or DLI), without sacrificing the effectiveness of the PDT treatment. These results are very surprising and contrary to the current understanding in the art.

According to the present invention, a low concentration formulation for photosensitizers (hereinafter referred to as "low concentration formulation") is provided for use in photodynamic therapy. The low concentration formulation contains substantially less photosensitizer per excipient volume than prior art photosensitizer compositions and medicaments used to treat the same or similar cancers. In a preferred embodiment, the low concentration formulation contains photosensitizers in an amount that is equal to $\frac{1}{50}$-$\frac{1}{3}$ of the photosensitizer present in known photosensitizer compositions presently used or under investigation for use in PDT.

Preferably, the low concentration formulation of the invention is suitable for intravenous injection and contains at least one excipient. Exemplary excipients include alcohol/propylene glycol mixtures, alcohols (such as ethanol), water/alcohol mixtures, and other solvents compatible with a given hydrophobic photosensitizer and non-toxic to patients. Specific excipient mixtures can be found to optimize the benefits of the low concentration formulations for groups of similarly hydrophobic photosensitizers. Suitable excipients for individual hydrophobic photosensitizers are generally known in the art.

A specific example of a low concentration formulation is provided for the photosensitizer meta-tetra(hydroxyphenyl) chlorin ("m-THPC"). The formulation comprises approximately 0.8 mg of m-THPC per 1 ml of the formulation, which is $\frac{1}{5}$ the concentration of the known m-THPC composition having a concentration of 4 mg/ml. Preferred excipients are propylene glycol and ethanol mixtures, especially in a v/v ratio of 3:2.

Use of the present low concentration formulation confers equivalent benefits of known, standard PDT procedures regardless of the method of administration. As such, the low concentration formulation of the invention may be administered by other methods, such as local injection and topical application. For administration via local injection and/or topical application, exemplary excipients include alcohol/propylene glycol mixtures alcohols, water/alcohol mixtures, alone or in combination with other solvents/additives known in the art to be useful for increasing, sustaining or controlling the PS solubility, and/or PS contact with or penetration of the skin.

It is well documented that systemic administration of high concentration photosensitizer formulations produces extensive side effects in patients. Thus, for PDT methods that entail systemic administration of PS, the advantages of the inventive low concentration formulation are readily apparent.

The low concentration formulation reduces or eliminates the most common side effects of PDT treatment. For instance, patients who receive the low concentration formulation of the present invention do not experience burning or other painful sensations that occur during the injection of known photosensitizer formulations. Furthermore, post-injection complications usually associated with high concentration formulations, i.e. phlebitis, lymphangitis and chemical burns, have not been observed after injection of the low concentration formulation of the present invention.

In some cases, it may be desirable to administer photosensitizers at a concentration that is substantially lower than the recommended concentration of known photodynamic medicaments in PDT treatments. Hereinafter this will be referred to as "low concentration therapy." For such low concentration therapies, the low concentration formulation of the invention is used in place of known photosensitizer formulations to administer at least one preselected dose of photosensitizer (mg/kg of body weight). The preselected dose may be equal to or less than the recommended dose that is administered in standard PDT using prior art photosensitizer compositions. The advantages of the inventive low concentration therapy method for PDT include a reduction in drug-light interval, a reduction in the duration and severity of skin photosensitization and more convenient administration of very low doses of photosensitizers.

A significant advantage of the low concentration formulation and the low concentration therapy method of the present invention lies in the shorter period of time needed for the photosensitizer to preferentially accumulate in hyperproliferating tissues to affect significant localized necrosis of diseased tissues, while clearing from normal tissue. Thus, when applied according to the formulation and method of the present invention, photosensitizers accumulate in diseased tissues more quickly and to a greater degree than PDT treatments using known photosensitizer compositions. As such, the low concentration formulation and low concentration therapy of the present invention reduces the time needed between injection and irradiation and thus shortens the overall PDT procedure. As a result, the present invention essentially can provide patients with a "same day" PDT treatment option that is more convenient and more comfortable than conventional PDT using known photosensitizer compositions.

The low concentration formulation and low concentration therapy of the present invention offers a unique and surprising post-treatment advantage over conventional, high concentration PDT treatments and known photosensitizer formulations as well. Use of the present low concentration formulation according to the low concentration therapy of the invention enables the photosensitizer to reduce to safe levels in normal tissues more rapidly after PDT treatment. Ordinarily, post-treatment retention of photosensitizer in healthy tissue, particularly the skin, is a major side-effect of conventional PDT and known photosensitizer compositions. Because the photosensitizer remains in tissue such as the skin for a substantial period of time after the photosensitizer is administered, exposure of the patient to sunlight, indoor light, or any other light source that contains the activation wavelength, can cause widespread and severe erythema. Patients must avoid sunlight and bright indoor light for up to 6 weeks or more after standard PDT dosing to allow the photosensitizer to reduce to safe levels in the skin. Patients must also wear protective clothing and sunglasses when spending time outdoors during this period of generalized skin photosensitivity. Use of the present invention in PDT treatments dramatically reduces the duration and severity of this side-effect.

The improved method of photodynamic therapy according to the present invention, defined previously as low concentration therapy, comprises the following steps:

1) Administering a preselected dose of a photosensitizer (in mg/kg body weight) to a treatment area by administering a low concentration formulation as described above;

2) Allowing sufficient time to elapse so that the photosensitizer preferentially accumulates in the target hyperproliferative tissues; and 3) Irradiating the treatment area with radiation having a wavelength that is absorbed by and activates the photosensitizer to form excited state singlet oxygen, which destroys hyperproliferative tissue proximate to the photosensitizer and oxygen.

The drug-light interval (DLI) in one embodiment of the present invention ranges from 5-48 hours after the administration of the photosensitizer. The exact DLI may vary between photosensitizers and specific treatments, which is generally known in the art. In another preferred embodiment of the inventive method, a DLI of 1-24 hours is optimal.

In other preferred embodiments, a low concentration therapy will involve the administration of photosensitizers at concentrations which are 67%-98% less than the concentrations of known photosensitizer compositions. As above, the drug-light interval is preferably between 1-24 hours to allow 'same day' or overnight treatments.

The present invention is further illustrated by the following examples, but is not limited thereby.

EXAMPLE 1

Comparison of Tissue Accumulation of m-THPC in Patients After Administration of the Standard m-THPC Formulation ("m-THPC") and a Low Concentration Formulation of m-THPC ("m-THPC-dl").

In this example, the two formulations were studied and compared to show m-THPC uptake in patient tissue after administration. The standard formulation ("m-THPC") contained the standard concentration of m-THPC for photodynamic therapy, which is 4 mg/ml. The second formulation ("m-THPC-dl") is a low concentration formulation containing 0.8 mg/ml of m-THPC. Each formulation was prepared with a mixture of pure propylene glycol and pure ethanol (3:2, v/v) as the excipient. Each patient received 0.05 mg of m-THPC per kg of body weight.

After administration of the two different formulations, the fluorescence accumulation in patients was monitored and a difference in the pharmacokinetics between the m-THPC and m-THPC-dl formulations was found. Surprisingly, fluorescence accumulation in tumor and perifocal skin was slower in patients treated with the standard (4 mg/ml) m-THPC formulation in the first day following intravenous injection. The results obtained are presented in the following tables.

| Fluorescence Detection After m-THPC (4 mg/ml) Formulation Injection | | | | | |
|---|---|---|---|---|---|
| | Time points (fluorescence found/# patients tested) | | | | |
| Measurement Points | 15 min | 1 hour | 3 hours | 1 day | 2 days |
| Tumor | 0/11 | 0/11 | 4/11 | All | All |
| Perifocal skin | 0/11 | 0/11 | 2/11 | 10/11 | All |
| Intact skin | 0/11 | 0/11 | 2/11 | 8/11 | 9/11 |

Fluorescence Detection After mTHPC-dl (0.8 mg/ml) Formulation Injection

| Measurement Points | Time points (fluorescence found/# patients tested) | | | | |
| --- | --- | --- | --- | --- | --- |
| | 15 min | 1 hour | 3 hours | 1 day | 2 days |
| Tumor | 0/16 | 5/16 | 12/16 | All | All |
| Perifocal skin | 0/16 | 2/16 | 11/16 | All | All |
| Intact skin | 0/16 | 0/16 | 10/16 | All | All |

As shown in the above tables, the m-THPC accumulated in tumors faster using the m-THPC-dl formulation (the "low concentration formulation") than the standard (4 mg/ml) m-THPC formulation. Specifically, at 1 hour after drug injection, m-THPC fluorescence was not detected in any patients treated with the standard (4 mg/ml) formulation, while in patients who received m-THPC-dl, measurable fluorescence had been observed in the tumors of over 30% of the patients. At 3 hours after injection a strong fluorescence was observed in the tumors of 75% of m-THPC-dl patients versus about 30% of patients in the standard (4 mg/ml) m-THPC group.

At 1 day after the injection fluorescence was observed in all points in the m-THPC-dl patients. In the standard (4 mg/ml) m-THPC group, there were patients where fluorescence in perifocal and intact skin was not observed even after 2 days post-injection. Within the period from 2 days to 3 weeks no significant difference in the pharmacokinetics was observed between the standard (4 mg/ml) m-THPC formulation and the low concentration formulation "m-THPC-dl."

EXAMPLE 2

Comparison of Tissue Accumulation of m-THPC in Patients After Administration of the Standard m-THPC Formulation ("m-THPC") and a Low Concentration Formulation when m-THPC is Diluted with Aqueous Lipid Containing Solubilizing Preparation Lipofundin®.

In this example, the two formulations were studied and compared to show m-THPC uptake in patient tissue after administration. The standard formulation ("m-THPC") contained the standard concentration of m-THPC for photodynamic therapy is 4 mg/ml. The second formulation ("m-THPC-Lipo") is a low concentration formulation containing 0.08 mg/ml of m-THPC (dilution for 50 times). It was prepared by the dilution of standard m-THPC solution with the concentration of 4 mg/ml by aqueous lipid containing solubilizing preparation. Lipofundin® MCT (10%, B. Braun Melsungen A G, Melsungen, Germany). Each patient received intravenously 0.05 mg of m-THPC per kg of body weight.

After administration of the two different formulations, the fluorescence accumulation in patients was monitored and a no difference in the pharmacokinetics between the m-THPC and m-THPC-Lipo formulations was found.

Fluorescence Detection After m-THPC (4 mg/ml) Formulation Injection

| Measurement Points | Time points (fluorescence found/# patients tested) | | | | |
| --- | --- | --- | --- | --- | --- |
| | 15 min | 1 hour | 3 hours | 1 day | 2 days |
| Tumor | 0/11 | 0/11 | 4/11 | All | All |
| Perifocal skin | 0/11 | 0/11 | 2/11 | 10/11 | All |
| Intact skin | 0/11 | 0/11 | 2/11 | 8/11 | 9/11 |

Fluorescence Detection After mTHPC-Lipo (0.08 mg/ml) Formulation Injection

| Measurement Points | Time points (fluorescence found/# patients tested) | | | | |
| --- | --- | --- | --- | --- | --- |
| | 15min | 1 hour | 3 hours | 1 day | 2 days |
| Tumor | 0/10 | 0/10 | 3/10 | All | All |
| Perifocal skin | 0/10 | 0/10 | 2/10 | 9/10 | All |
| Intact skin | 0/10 | 0/10 | 1/10 | 9/10 | All |

As shown in the above tables, the m-THPC accumulated in tumors proceeds similarly with the use of standard m-THPC formulation with the concentration 4 mg/ml of drug and with the use of diluted form m-THPC-Lipo having the drug concentration of 0.08 mg/ml. Particularly, the profile of m-THPC accumulation in tumors within first 24 hours after drug injection (most important period for practical use of m-THPC) had no principal difference for both formulations in spite of very different concentration of m-THPC in both formulations used.

These results bear strong evidence to the uniqueness and unexpected results observed in Example 1 with the "m-THPC-DL" formulation. Since the excipient in Example 2 is generally understood to be a better 'solvent' for molecules of hydrophobic photosensitizers than the special solvent mixture found in Example 1, it is thus surprising to have such striking results in accumulation within tumor tissue with the special solvent mixture.

Having described preferred embodiments of the invention with reference to the accompanying examples, it is to be understood that the invention is not limited to the precise embodiments, and that various changes and modifications may be effected therein by those skilled in the art without departing from the scope or spirit of the invention as defined in the appended claims.

What is claimed is:

1. A low concentration photosensitizer formulation useful for systemic and other applications of photodynamic therapy of hyperproliferative tissue disease with specially enhanced pharmacokinetics and pharmacodynamics, comprising;

a hydrophobic photosensitizer in an alcoholic excipient mixture comprising propylene glycol and ethanol which solubilizes said hydrophobic photosensitizer;

and aqueous fluid;

wherein said photosensitizer is meta-tetra(hydroxyphenyl) chlorin (m-THPC); and wherein said photosensitizer is present in a concentration of 0.08 mg/ml to 1.3 mg/ml in said alcoholic excipient mixture.

2. The low concentration formulation according to claim 1, wherein said m-THPC is present in an amount ranging from about 0.08 mg/ml to 0.8 mg/ml.

3. The low concentration formulation according to claim 1, wherein said alcoholic excipient mixture is propylene glycol and ethanol in a v/v ratio of 3:2.

4. A method of low concentration therapy for the PDT treatment of disease comprising the steps of:

a. administering at least one preselected dose of a photosensitizer in a low concentration formulation as described in claim 1;

b. allowing a period of time to allow said photosensitizer to preferentially accumulate in hyperproliferative tissue, generally less than 48 hours; and
c. applying radiation to said treatment area having a properly selected wavelength to activate said photosensitizer and render said photosensitizer toxic to tissue.

5. The method according to claim 4 wherein said period of time allowed is between 1-24 hours.

6. The method of claim 4 wherein said PDT treatment is started and completed within a 24 hour period.

* * * * *